(12) United States Patent
Schweikert et al.

(10) Patent No.: US 7,344,527 B2
(45) Date of Patent: Mar. 18, 2008

(54) LUER WITH INTEGRATED CLAMP

(75) Inventors: Timothy Schweikert, Levittown, PA (US); William L. Bartow, Bryn Mawr, PA (US); Charles M. Bartish, Jr., Providence, RI (US)

(73) Assignee: Medical Components, Inc., Harleysville, PA (US)

( * ) Notice: Subject to any disclaimer, the term of this patent is extended or adjusted under 35 U.S.C. 154(b) by 94 days.

(21) Appl. No.: 10/991,708

(22) Filed: Nov. 18, 2004

(65) Prior Publication Data

US 2005/0107770 A1    May 19, 2005

Related U.S. Application Data

(60) Provisional application No. 60/523,422, filed on Nov. 19, 2003.

(51) Int. Cl.
*A61M 25/16*    (2006.01)

(52) U.S. Cl. .......................... 604/533; 604/250

(58) Field of Classification Search ........ 604/533–539, 604/167.01–167.06, 245–246, 250, 256
See application file for complete search history.

(56) References Cited

U.S. PATENT DOCUMENTS

| | | | |
|---|---|---|---|
| 4,429,852 A * | 2/1984 | Tersteegen et al. ............ | 251/9 |
| 4,451,257 A | 5/1984 | Atchley | |
| 4,889,527 A | 12/1989 | Herrli | |
| 4,950,255 A | 8/1990 | Brown et al. | |
| 5,186,714 A | 2/1993 | Boudreault et al. | |
| 5,396,925 A | 3/1995 | Poli | |
| 5,429,616 A * | 7/1995 | Schaffer ............ | 604/250 |

(Continued)

OTHER PUBLICATIONS

International Search Report, PCT/US2004/39018, Dec. 30, 2005, (one page)

(Continued)

*Primary Examiner*—Nicholas Lucchesi
*Assistant Examiner*—Theodore J Stigell
(74) *Attorney, Agent, or Firm*—Anton P. Ness; Fox Rothschild, LLP

(57) ABSTRACT

A tubing connector (100) having a body (132) that has a first end (134) having a first opening (138) and a second end (136) having a second opening (140). A passageway (142) extends through the body between the first opening and the second opening. A side opening (144) includes a first side wall (146), an opposing second side wall (148) and a latch catch (150) disposed between the first and second side walls, and extends from the passageway (142) through the body (132) as a breach opening. The connector also has a clamping member (160), having a first clamping end (162) that is hingedly connected to the body (132) and a second clamping end (168) that is adapted to releasably engage the latch catch (150). A clamp portion (172) is disposed between the first clamping end (162) and the second clamping end (168), and protrudes into passageway (142) to compress closed a tubing, such as a catheter lumen, (112) extending through the tubing connector, when the clamping member (160) is in the closed position, and is releasable from the latch catch (150) and disengages from the catheter.

21 Claims, 2 Drawing Sheets

U.S. PATENT DOCUMENTS

| | | | |
|---|---|---|---|
| 5,549,657 A | 8/1996 | Stern et al. | |
| 5,749,859 A * | 5/1998 | Powell | 604/167.03 |
| 5,921,968 A | 7/1999 | Lampropoulos et al. | |
| 5,928,200 A | 7/1999 | Thorne et al. | |
| 6,482,180 B2 * | 11/2002 | Toyokawa et al. | 604/165.03 |

OTHER PUBLICATIONS

Written Opinion, PCT/US2004/39018, Dec. 30, 2005, (three pages)
International Preliminary Report. PCT/US2004/039018 dated Jun. 1, 2006 (5 pages).

* cited by examiner

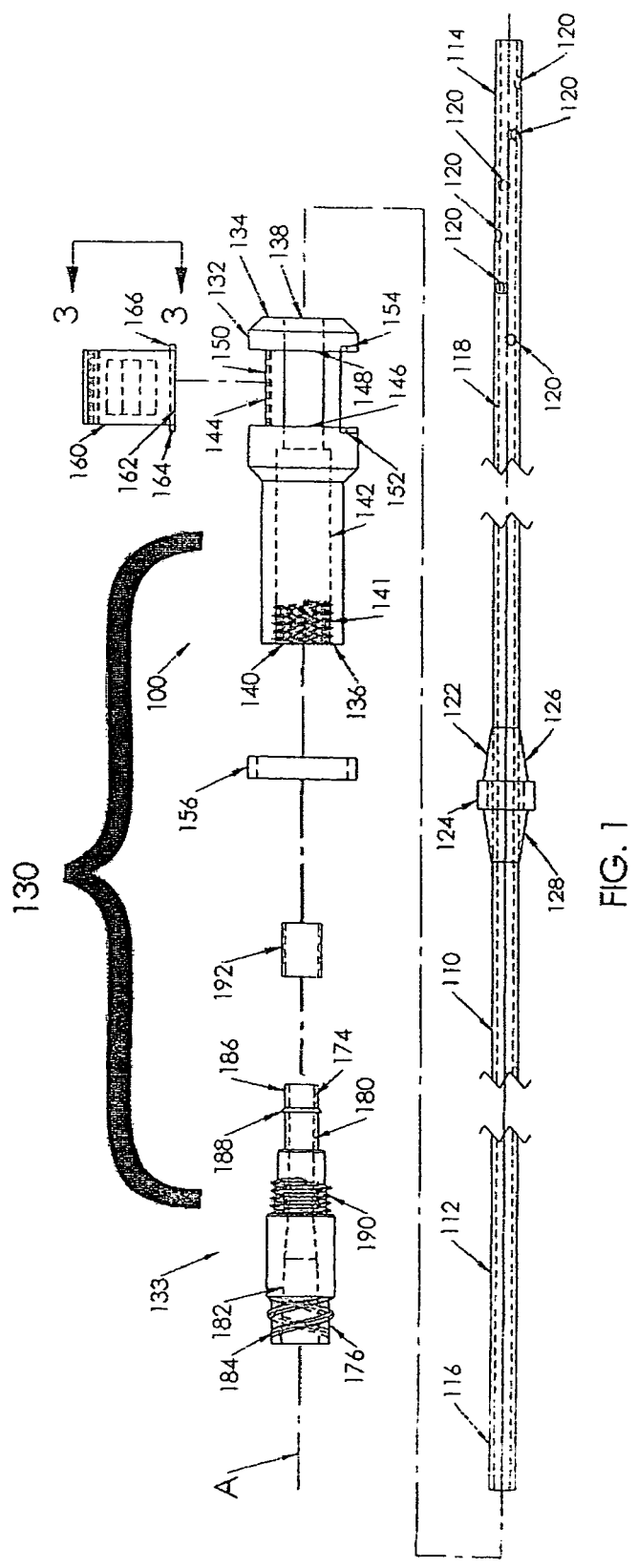
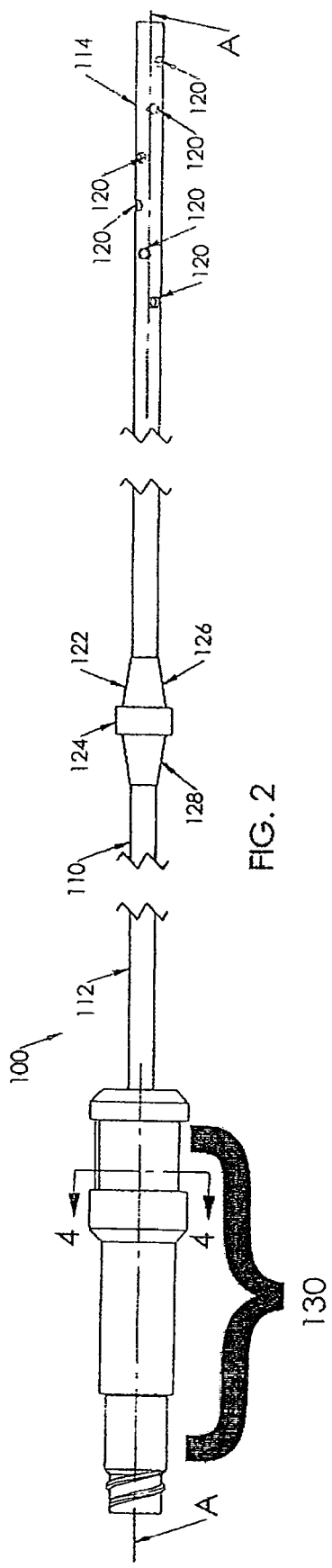
FIG. 1
FIG. 2

LUER WITH INTEGRATED CLAMP

CROSS REFERENCE TO RELATED APPLICATION

The present application claims the benefit of U.S. Provisional Patent Application Ser. No. 60/523,422 filed on Nov. 19, 2003.

FIELD OF THE INVENTION

The present invention relates to a catheter luer with an integrated lock. The integrated lock provides an additional sealing feature for the luer.

BACKGROUND OF THE INVENTION

Catheters may be located in various venous locations and cavities throughout the body of a patient for introduction of fluids to a body or removal of fluids from a body. Such catheterization may be performed by using single lumen catheters or, in an instance where it is desirable to remove fluids from a body and return fluids to a body at the same time, by using multiple single lumen catheters or a multiple lumen catheter.

Generally, to insert any catheter into a blood vessel, the vessel is identified by aspiration with a long hollow needle in accordance with the well known Seldinger technique. When blood enters a syringe attached to the needle, indicating that the vessel has been found, a thin guidewire is then introduced, typically through a syringe needle or other introducer device into the interior of the vessel. The introducer device is then removed, leaving the guidewire within the vessel. The guidewire projects beyond the surface of the skin. At this point, several options are available to a physician for catheter placement. The simplest is to pass a catheter into the vessel directly over the guidewire. The guidewire is then removed, leaving the catheter in position within the vessel. However, this technique is only possible in cases where the catheter (for example, a small diameter dual lumen catheter) is of a relatively small diameter, made of a stiff material, and not significantly larger than the guidewire. If the catheter to be inserted is significantly larger than the guidewire, a dilator device containing a sheath is passed over the guidewire to enlarge the opening in the vessel. The dilator is then removed along with the guidewire, leaving the sheath in place, and the catheter is then passed through the sheath into the vessel. The guidewire is then removed, leaving the catheter in position within the vessel.

Each catheter lumen is typically fluidly connected to an extracorporeal treatment device, such as a hemodialysis machine, or some other device used for injecting fluids into the body and/or removing fluids from the body. Each lumen is typically connected to the extracorporeal treatment device using a standard connector at its proximal end. Such standard connectors are commonly referred to as "luers." A luer is a standard fitting that accommodates the fluid connection of the lumen to an extracorporeal treatment device, such as the hemodialysis machine, as well as a cap or an infuser for medicaments. Generally, during hemodialysis treatment, the catheter luer is releasably connected to a mating luer that is in fluid communication with the hemodialysis machine. Preferably, between treatments, it is desirable to restrict the flow of air, blood and contaminants through the catheter. Generally, after a luer is disconnected from the mating luer of a hemodialysis machine, the luer is capped. In the time period between removal of the mating luer of a hemodialysis machine and the securing of a cap onto the catheter, the catheter luer is uncovered and there is no structure to restrict the flow of air, blood and contaminants through the catheter, in which case the physician must manually close off the luer opening.

It would be desirable to provide a luer connection that securely connected the luer to the catheter and provided a means for restricting flow through the catheter. Further, it would be desirable to provide an assembly for connecting a luer to a lumen that integrates a secure connection and a releasable clamping mechanism to restrict flow through the lumen when the catheter is not in use.

BRIEF SUMMARY OF THE INVENTION

The present invention provides a tubing connector. The tubing connector comprises a body that has a first end having a first opening, and a second end having a second opening. A passageway extends through the body between the first opening and the second opening. A side opening or breach extends from the passageway through the body and includes a first side wall, an opposing second side wall and a latch catch disposed between the first and second side walls. The body also has a cannula extending into the passageway from the first end toward the second end. The side opening is disposed between the cannula and the second end. The connector also has a clamping member, having a first clamping end that is hingedly connected to the body, and a second clamping end that is adapted to releasably engage the latch catch. A clamp portion is disposed between the first clamping end and the second clamping end.

The present invention also provides a tubing connector comprising a first end, a second end and a longitudinal axis extending therethrough between the first end and the second end. The tubing connector further comprises a tubular body extending between the first end and the second end and a longitudinal passageway extending along the longitudinal axis between the first end and the second end. The longitudinal passageway is defined by the tubular body. The tubing connector further comprises a side opening extending from the longitudinal passageway through the tubular body, in a direction that is generally perpendicular to the longitudinal axis. The side opening is defined by a first side wall and a second side wall. The tubing connector further comprises a clamping member that is disposed within the side opening. The clamping member is disposable in an open position and a closed position. The clamping member is pivotable about an axis that is generally parallel to the longitudinal axis.

The present invention further provides a catheter assembly comprising a tubing connector. The tubing connector has a body comprising a first end, having a first opening, and a second end, having a second opening. A passageway extends through the body between the first opening and the second opening. The tubing connector also has a side opening extending from the passageway through the body. The side opening includes a first side wall, an opposing second side wall and a latch catch disposed between the first side wall and the second side wall. A cannula extends into the passageway from the first end toward the second end. The side opening is disposed between the cannula and the second end. The tubing connector further comprises a clamping member. The clamping member has a first clamping end hingedly connected to the body, a second clamping end and a clamp portion disposed between the first clamping end and the second clamping end. The second clamping end has a latch adapted to releasably engage the latch catch. The catheter assembly further comprises a catheter lumen. The catheter lumen has a proximal end that is in fluid communication with the cannula. The catheter lumen extends from the second end of the body. The clamping member is adapted to clamp the catheter lumen to releasably restrict fluid flow in the catheter lumen between the cannula and the second end of the body.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is an exploded side view of a catheter assembly incorporating a luer clamp according to a preferred embodiment of the present invention.

FIG. 2 is a side view of the assembled catheter assembly shown in FIG. 1.

DETAILED DESCRIPTION OF THE INVENTION

Figure 5:
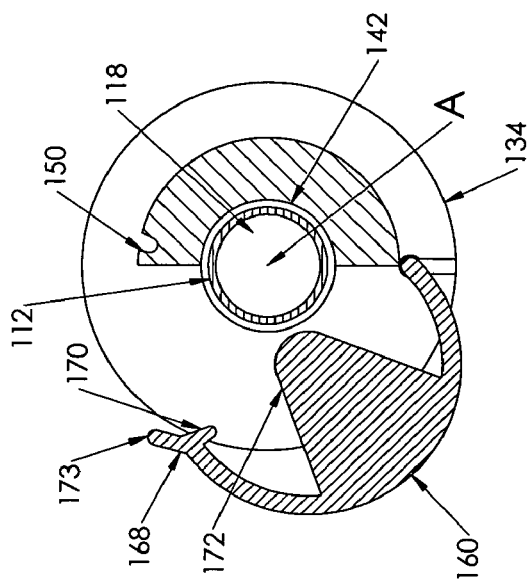
FIG. 5 is a sectional view of the luer clamp, of FIG. 4, in an open position.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of a catheter connected to a connecting luer according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring to FIG. 1, an exploded view of a catheter assembly 100 according to the present invention is shown. The catheter assembly 100 includes a catheter 110 and a luer 130 having an integrated sealing device. An assembled view of the catheter assembly 100 is shown in FIG. 2. As shown in FIGS. 1 and 2, there is a longitudinal axis "A" extending through the catheter assembly 100. When assembled, as shown in FIG. 2, the catheter 110 and the luer 130 are coaxial along the axis "A".

The catheter 110 includes a body 112 having a distal end 114 and a proximal end 116. Preferably, the catheter is constructed from a biocompatible material, such as TECOFLEX® polyurethane, although those skilled in the art will recognize that other suitable biocompatible materials may be used. An internal lumen 118 extends longitudinally, about the axis "A," through the body 112 from the distal end 114 to the proximal end 116. A plurality of side openings 120 extend through the body 112 proximate to the distal end 114. Each of the plurality of side openings 120 communicates the internal lumen 118 with the exterior of the body 112. While the catheter assembly 100 shown here comprises a catheter body 112 with a single lumen 118, it will be well known to those skilled in the art that the luer 130 having an integrated sealing device may be connected to each lumen of multiple lumen catheters, or to any other flexible fluid conduit that is sufficiently resilient to resist failure when deformed through clamping.

Preferably, a cuff assembly 122 is disposed along the body 112 between the distal end 114 and the proximal end 116 of the body 112. The cuff assembly 122 includes a cuff 124, which is made from a fibrous material, such as polyester. One preferred material for the cuff 124 is DACRON® polyester. The cuff assembly 122 further includes a generally frusto-conically shaped distal tapered portion 126 that tapers inward from the cuff 124 to the body 112 of the catheter 110 distal of the cuff 124 and a generally frusto-conically shaped proximal tapered portion 128 that tapers inward from the cuff 124 to the body of the catheter 110 proximal of the cuff 124.

The luer 130 is adapted to releasably connect to the proximal end 116 of the body 110. The luer 130 includes a body 132 and a luer-cannula assembly 133. Preferably, the luer 130 is constructed from titanium, although those skilled in the art will recognize that the luer 130 may be constructed from other suitable materials as well. The body 132 has a distal end 134 and a proximal end 136. The distal end 134 includes a distal opening 138 and the proximal end 136 includes a proximal opening 140. Preferably, the proximal opening 140 includes female threads 141 for connecting the body 132 with the luer-cannula assembly 133. A passageway 142 extends longitudinally, about the axis "A," through the body 132 between the distal opening 138 and the proximal opening 140.

A generally rectangularly shaped side opening or breach 144 extends from the passageway 142 through the body 132, beginning at the passageway 142, and extending in a direction that is perpendicular to the longitudinal axis "A." The side opening 144 is defined by a first side wall 146, and an opposing second side wall 148. Preferably the first side wall 146 is a generally planar surface that is generally perpendicular to the longitudinal axis "A." Preferably, the second side wall 148 is also a generally planar surface that is generally perpendicular to the longitudinal axis "A" and disposed at a point along the longitudinal axis "A" that is distal from the first side wall 146. Preferably, the side opening 144 includes a latch catch 150 that extends, in a direction that is generally perpendicular to the longitudinal axis "A," between the first side wall 146 and the second side wall 148 (see FIG. 4). Preferably, a first hinge opening 152 extends from the side opening 144, through the first side wall 146 and proximally into the body 132. Likewise, a second hinge opening 154 preferably extends from the side opening 144, distally into the body 132 through the second side wall 148.

Figure 3:
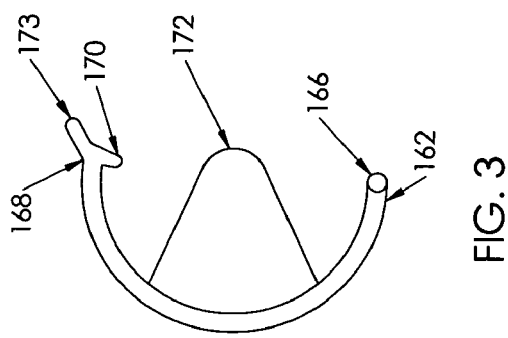
FIG. 3 is a distal end view of a clamping member of the luer clamp taken along lines 3-3 of FIG. 1.
Figure 4:
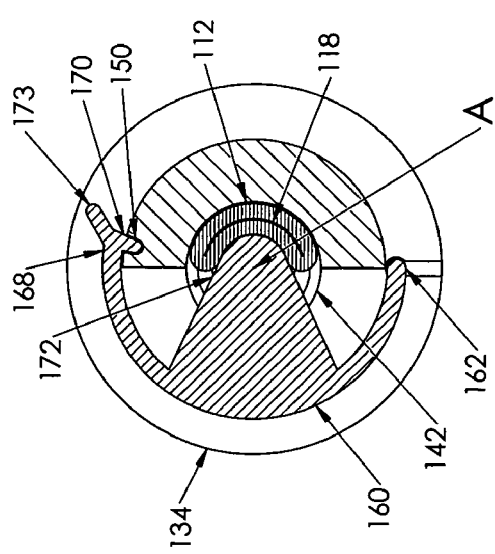
FIG. 4 is a sectional view of the luer clamp in a closed position, taken along lines 4-4 of FIG. 2.

Referring to FIGS. 1 and 3-5, a clamping member 160 has a first clamping end 162 with a first hinge pin 164 adapted to extend into the first hinge opening 152 and a second hinge pin 166 adapted to extend into the second hinge opening 154. The clamping member 160 further includes a second clamping end 168 opposite the first clamping end 162. The second clamping end 168 includes a latch 170 that is sized to releasably engage the latch catch 150 when the clamping member 160 is in a closed position. The second clamping end 168 further includes an opening tab 173. A generally curved clamp portion 172 that extends from the clamping member 160 between the first clamping end 162 and the second clamping end 168. The rounded end of clamp portion 172 is sized slightly smaller than the passageway 142 of the body 132. Preferably, when the clamping member 160 is in the closed position, there is enough space between the curved clamp portion 172 and the interior wall of the passageway 142 to retain the catheter lumen 110 in a compressed state, thereby restricting flow through the lumen 110. As shown in FIG. 4, in order to compress the catheter lumen, the clamping member 160 is of generally nondeformable material and is preferably constructed from nylon, although those skilled in the art will recognize that the clamping member may be constructed from other suitable materials as well.

As shown in FIG. 1, a sliding lock 156 may be slidably disposed about the body 132. Preferably, the sliding lock 156 is sized to slidingly engage the exterior surface of the body 132. The sliding lock 156 is adapted to slide over the body 132 and the clamping member 160 when the clamping member 160 is in the closed position, thereby restraining the clamping member 160 in the closed position. Preferably the sliding lock 156 is constructed from any material that is resilient enough to resist deformation when slid over the locking member 160.

Referring now to FIGS. 1 and 2, the luer-cannula assembly 133 includes a distal end 174, a proximal end 176, and a through passageway 180 extending, along the longitudinal axis "A," between the distal end 174 and the proximal end 176. A proximal end of the through passageway 180 includes a tapered male luer connection 182 sized to frictionally and sealingly mate with a connector having a tapered female luer connection (not shown), such as one connected to a hemodialysis machine. Preferably a set of male threads 184 are disposed about the proximal end 176 of the luer-cannula assembly 133. The male threads 184 are preferably adapted to engage female threads (not shown) that are disposed on the connector having a tapered male luer connection (not shown). The distal end 174 of the luer-cannula assembly 133 also includes a male threaded connection 190 adapted to mate to the female threads 141 of the body 132, for further securing the connector to the luer-cannula assembly 133.

The distal end 174 includes a luer cannula 186 having an outer diameter sized to frictionally fit within the internal lumen 118. Optionally, a barb 188 may be disposed on the luer cannula 186 to help retain the internal lumen 118 on the luer cannula 186.

A compression ring 192 is disposed over the proximal end 116 of the catheter 110 and within the body 132 of the luer-cannula assembly 130 to further frictionally retain the proximal end 116 of the catheter 110 onto the luer cannula 186.

As shown in FIGS. 1 and 3-5, to assemble the catheter assembly 100, a first clamping end 162 of the clamping member 160 is inserted into the side opening 144 by inserting the first hinge pin 164 into the first hinge opening 152 and the second hinge pin 166 into the second hinge opening 154. The body 132 is slid over the proximal end 116 of the catheter 110. The compression ring 192 is next slid over the proximal end 116 of the catheter 110. The luer cannula 186 is inserted into the internal lumen 118 at the proximal end 116 of the catheter 110. The compression ring 192 is then slid proximally along the catheter 110 until it is disposed about the proximal end 116 of the catheter 110 and the luer cannula 186. The male threads 190 of the luer-cannula assembly 133 are threadingly engaged with the female threads 141 of the body 132 by rotating the body 132 about the luer-cannula assembly 133.

The clamping member 160 may be rotated to a closed position, as shown in FIGS. 3-5, by the clamping member 160 about the hinge pins 164, 166 until the latch 170 engages the latch catch 150, securing the clamping member 160 in a closed position. The clamp portion 172 engages the catheter 110 and compresses the catheter 110 as shown in FIG. 4, restricting fluid flow through the catheter 110.

To allow fluid flow through the catheter 110, the latch 170 is rotated from right to left as viewed in FIG. 4, about the hinge pin 166. The latch 170 is released from the latch catch 150 by biasing the latch tab 173 from right to left as shown in FIG. 4. The clamping member 160 is rotated from right to left as shown in FIG. 4 about the hinge pins 164, 166. The catheter 110, because of its elastic nature, opens to the position shown in FIG. 5, allowing fluid flow through the catheter 110.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A tubing connector comprising:
   a body having a first end having a first opening, a second end having a second opening, a passageway extending through the body between the first opening and the second opening wherein the second opening is adapted to receive insertably thereinto a tubing end portion, and a side opening extending from the passageway through the body, wherein the side opening includes a first side wall, an opposing second side wall, and a latch catch disposed between the first side wall and the second side wall;
   a luer-cannula assembly having a cannula extending into the passageway from the first end toward the second end and adapted for the tubing end portion to be secured thereto within the body, wherein the side opening is disposed between the cannula and the second end; and
   a discrete clamping member of generally nondeformable material and having a first clamping end hingedly connected to the body along a hinge axis parallel to the passageway, a second clamping end having a latch adapted to releasably engage the latch catch of the body, and a clamp portion extending between the first clamping end and the second clamping end that is adapted to protrude into the passageway to compress closed the tubing end portion extending through the passageway, when the clamping member is in the closed position.

2. The connector according to claim 1, wherein the first clamping end is hingedly connected to each of the first side wall and the second side wall and is rotatable about the hinged connection.

3. The connector according to claim 1, wherein the luer-cannula assembly is releasably connected to the first end of the body.

4. The connector according to claim 3, wherein the luer-cannula assembly is threadably connected to the first end of the body.

5. The connector according to claim 1, wherein the luer-cannula assembly further comprises a proximal end having a threaded connection section for releasably connecting to an external device.

6. The connector according to claim 5, wherein the external device is a cap.

7. The connector according to claim 5, wherein the external device is a hemodialysis machine.

8. The connector according to claim 1, further comprising a sliding lock, slidably disposed about the body.

9. A tubing connector comprising:
a first end, a second end, and a longitudinal axis extending therethrough between the first end and the second end;
a tubular body extending between the first end and the second end;
a longitudinal passageway extending along the longitudinal axis between the first end and the second end, wherein the longitudinal passageway is defined by the tubular body;
a side opening extending from the longitudinal passageway through the tubular body, in a direction that is generally perpendicular to the longitudinal axis, wherein the side opening is defined by a first side wall and a second side wall; and
a discrete clamping member of generally nondeformable material having a first clamping end hingedly disposed within the side opening, wherein the clamping member is disposable in an open position and a closed position, wherein the clamping member is pivotable around an axis that is generally parallel to the longitudinal axis and includes a tube-engaging clamping portion that is adapted to protrude into the passageway to compress closed a tubing extending through the passageway, when the clamping member is in the closed position, and further includes a latch at a second clamping end that is releasably engageable with a latch catch of the body adjacent to the side opening to maintain the clamping member in the closed position.

10. The tubing connector according to claim 9, further comprising a sliding lock, slidably disposed about the body.

11. The tubing connector according to claim 9, wherein the tubing connector further comprises a proximal portion and a distal portion, wherein the distal portion includes the side opening, and wherein the proximal portion is releasably connected to the distal portion.

12. The tubing connector according to claim 11, wherein the proximal portion has a connection section for releasably connecting an external device to the connector.

13. The tubing connector according to claim 12, wherein the external device is a cap.

14. The tubing connector according to claim 13, wherein the external device is a hemodialysis machine.

15. A catheter assembly comprising:
a catheter having a lumen defining a lumen passageway and having a proximal end; and
a tubing connector including:
a body having a first end having a first opening, a second end having a second opening adapted to receive thereinto the catheter lumen proximal end, a passageway extending through the body between the first opening and the second opening, and a side opening extending from the passageway through the body, wherein the side opening includes a first side wall, an opposing second side wall, and a latch catch disposed between the first side wall and the second side wall;
a luer-cannula assembly having a cannula extending into the passageway from the first end toward the second end and is adapted to be secured to the catheter lumen proximal end, wherein the side opening is disposed between the cannula and the second end; and
a discrete clamping member of generally nondeformable material and having a first clamping end hingedly connected to the body along a hinge axis parallel to the passageway, a second clamping end having a latch adapted to releasably engage the latch catch of the body when pivoted into a clamping state, and a clamp portion disposed between the first clamping end and the second clamping end; and
the catheter lumen proximal end being in fluid communication with the cannula and extending from the second end of the body,
wherein the clamping member is adapted to clamp the catheter lumen to releasably restrict fluid flow in the catheter lumen passageway between the cannula and the second end of the body.

16. The catheter assembly according to claim 15, wherein the first clamping end is hingedly connected to each of the first side wall and the second side wall and is rotatable about the hinged connection.

17. The catheter assembly according to claim 15, wherein the luer-cannula assembly is threadably connected to the second end of the body.

18. The catheter assembly according to claim 15, wherein the first end further comprises a proximal end having a threaded connection section for releasably connecting an external device to the connector.

19. The catheter assembly according to claim 18, wherein the external device is a cap.

20. The catheter assembly according to claim 18, wherein the external device is a hemodialysis machine.

21. The catheter assembly according to claim 15, further comprising a sliding lock, slidably disposed about the body.

* * * * *